(12) United States Patent
Plouf et al.

(10) Patent No.: US 7,803,121 B2
(45) Date of Patent: Sep. 28, 2010

(54) IMPLANT TRANSMITTER

(75) Inventors: Peter Plouf, London (CA); Blair Poetschke, London (CA); Milan Placko, London (CA); Kim Wood, London (CA); Mohammad Maymandi-Nejad, Waterloo (CA)

(73) Assignee: Scisense Inc., London (CA)

( * ) Notice: Subject to any disclaimer, the term of this patent is extended or adjusted under 35 U.S.C. 154(b) by 898 days.

(21) Appl. No.: 11/207,705

(22) Filed: Aug. 22, 2005

(65) Prior Publication Data

US 2007/0043298 A1 Feb. 22, 2007

(51) Int. Cl.
*A61B 5/02* (2006.01)
*A61B 5/05* (2006.01)

(52) U.S. Cl. .................. 600/486; 600/481; 600/508; 600/547

(58) Field of Classification Search .................. 600/486, 600/547, 561
See application file for complete search history.

(56) References Cited

U.S. PATENT DOCUMENTS

| | | | |
|---|---|---|---|
| 3,490,441 A | 1/1970 | Curtis | |
| 3,710,781 A | 1/1973 | Hutchins, IV et al. | |
| 3,724,274 A | 4/1973 | Millar | |
| 3,748,623 A | 7/1973 | Millar | |
| 4,124,023 A | 11/1978 | Fleischmann et al. | |
| 4,141,253 A | 2/1979 | Whitehead, Jr. | |
| 4,274,423 A | 6/1981 | Mizuno et al. | |
| 4,281,667 A | 8/1981 | Cosman | |
| 4,407,296 A | 10/1983 | Anderson | |
| 4,456,013 A | 6/1984 | De Rossi et al. | |
| 4,519,401 A | 5/1985 | Ko et al. | |
| 4,557,269 A | 12/1985 | Reynolds et al. | |
| 4,722,348 A | 2/1988 | Ligtenberg et al. | |
| 4,796,641 A | 1/1989 | Mills et al. | |
| 4,846,191 A | 7/1989 | Brockway et al. | |
| 4,901,731 A | 2/1990 | Millar | |
| 4,945,762 A * | 8/1990 | Adamic, Jr. ............ | 73/862.622 |
| 5,113,869 A * | 5/1992 | Nappholz et al. ........... | 600/508 |
| 5,218,965 A | 6/1993 | Ring | |

(Continued)

FOREIGN PATENT DOCUMENTS

WO WO 0219905 A1 3/2002

*Primary Examiner*—Patricia C Mallari
(74) *Attorney, Agent, or Firm*—Brett J. Slaney; John R. S. Orange; Blake, Cassels & Graydon LLP (57) ABSTRACT

A monitoring system is provided that enables the monitoring of a heart in a living organism by continuously measuring both pressure and volume in a chamber of the heart, preferably the left ventricle (LV). The pressure and volume measurements are acquired using a single sensing tip and are communicated to a transmitting device to be wirelessly transmitted to a receiving device, wherein they are used to monitor the heart. The system may also incorporate a temperature measurement that can be transmitted with the volume and pressure measurement to provide further data for monitoring. The system may also extract an electrocardiogram (ECG) signal from the volume measurement. This allows the monitoring of up to four signals that can be used to determine the beat by beat state of cardiac output and any changes caused by disease or therapy. In addition to a compact design, the system may also incorporate an energy saving timing scheme that reduces the power required per acquisition cycle and thus increases the operational lifetime of the transmitting device.

21 Claims, 11 Drawing Sheets

U.S. PATENT DOCUMENTS

| | | |
|---|---|---|
| 5,431,628 A | 7/1995 | Millar |
| 5,535,752 A * | 7/1996 | Halperin et al. ............. 600/483 |
| 5,842,998 A | 12/1998 | Gopakumaran et al. |
| 5,866,821 A * | 2/1999 | Raynes ........................ 73/708 |
| 5,882,312 A | 3/1999 | Gopakumaran et al. |
| 5,902,248 A | 5/1999 | Millar et al. |
| 5,971,933 A | 10/1999 | Gopakumaran et al. |
| 6,033,366 A | 3/2000 | Brockway et al. |
| 6,112,115 A | 8/2000 | Feldman et al. |
| 6,141,590 A * | 10/2000 | Renirie et al. ................. 607/20 |
| 6,296,615 B1 | 10/2001 | Brockway et al. |
| 6,394,986 B1 | 5/2002 | Millar |
| 6,409,674 B1 | 6/2002 | Brockway et al. |
| 6,494,832 B1 * | 12/2002 | Feldman et al. ............. 600/301 |
| 6,740,033 B1 | 5/2004 | Olejniczak et al. |
| 6,865,419 B2 | 3/2005 | Mulligan et al. |
| 6,926,674 B2 | 8/2005 | Tenerz et al. |
| 2002/0035331 A1 | 3/2002 | Brockway et al. |
| 2002/0065472 A1 | 5/2002 | Brockway et al. |
| 2002/0138009 A1 | 9/2002 | Brockway et al. |
| 2003/0074035 A1 | 4/2003 | Bornhoft et al. |
| 2004/0147969 A1 * | 7/2004 | Mann et al. .................... 607/17 |
| 2004/0254436 A1 * | 12/2004 | Sunagawa et al. ........... 600/374 |

* cited by examiner

IMPLANT TRANSMITTER

FIELD OF THE INVENTION

The present invention relates generally to data acquisition systems and particularly to acquiring data from a heart in a living organism.

DESCRIPTION OF THE PRIOR ART

In the field of cardiac research the standard test for measuring cardiac efficiency is the pressure volume graph. This test correlates Left Ventricle (LV) chamber pressure and volume as the heart contracts and expands. Pressure and volume values are important for quantifying efficiency in any pump system, and can be used to calculate volumetric efficiency of such systems. Cardiac efficiency is a useful measurement for studying heart disease, by quantifying the progress of the disease and measuring the effectiveness of the treatment.

Recently, gene altered mice have increased in popularity as a means for studying heart disease, and for modelling human heart disease. Typically, LV data is measured using a catheter that is inserted into the LV. The catheter typically has separate instrumentation for measuring blood pressure and blood volume. There are several drawbacks to using data taken from anaesthetized mice, most significantly the fact that it has been found that cardiovascular data taken from an anaesthetized specimen differs significantly from free-roaming specimens.

In order to measure cardiovascular data from a free-roaming specimen, an implanted device is required that can operate while the specimen is active, and transmit data to the exterior of the specimen for processing. This need presents several design problems, notably size and battery life. Particularly, a reduced size provides a less invasive device, and a longer battery life decreases the number of surgical operations required to change or recharge a device. The need to reduce repeated trauma due to surgery and the cost of the surgery are driving reasons for the need to extend battery life in biological implants. These concerns are heightened when extending the application to human specimens.

There are numerous devices that have been developed for measuring physiological pressure in living specimens, e.g., those shown in U.S. Pat. Nos. 4,796,641; 4,846,191; and 6,033,366. These devices include a catheter having a pressure sensor that is inserted into an area in the specimen having a physiological pressure, such as an artery. The sensors include a pressure transmitting catheter filled with a pressure transmitting fluid. A pressure transducer communicates with the fluid to provide an electric pressure signal representing variations in physiological pressure that can be transmitted to the exterior of the specimen. These devices are only concerned with measuring pressure, and the use of a fluid filled catheter can lead to undesirable frequency response characteristics and may exhibit head pressure artefacts.

Other devices, e.g., that shown in U.S. Pat. No. 6,409,674 provide an implantable sensor being anchored to the interior wall of the LV in a living specimen. The sensor acquires and transmits data from within the heart to an external data receiver. This device is concerned with only measuring a single parameter, and specifically illustrates measuring pressure.

There exists a need for an implantable data acquisition device to acquire more comprehensive cardiovascular data, which presents minimal invasiveness and has a prolonged battery life.

It is therefore an object of the present invention to obviate or mitigate at least one of the above-mentioned disadvantages.

SUMMARY OF THE INVENTION

In one aspect, the present invention provides a method of monitoring a heart of a living organism comprising the steps of situating a sensing tip within a chamber of the heart, the sensing tip extending through the chamber and comprising a pressure sensing device and a volume sensing device; obtaining a pressure measurement and a volume measurement in the chamber using the pressure sensing device and the volume sensing device respectively; communicating the measurements to a transmitting device; and wirelessly transmitting electrical representations of the measurements to a receiving device, the electrical representations being used to monitor the heart.

In another aspect, the present invention provides a system for monitoring a heart of a living organism comprising a sensing tip situated within a chamber of the heart and extending therethrough, the sensing tip comprising a pressure sensing device and a volume sensing device, the pressure sensing device adapted to obtain a pressure measurement in the chamber, the volume sensing device adapted to obtain a volume measurement in the chamber, and the sensing tip adapted for communicating the measurements; a transmitting device for receiving the measurements from the sensing tip, the transmitting device being adapted to wirelessly transmit electrical representations of the measurements; and a receiving station for receiving the electrical representations, the electrical representations being used to monitor the heart.

In yet another aspect, the present invention provides a method for obtaining an intracardiac electrocardiogram signal comprising the steps of measuring a conductance signal from a heart chamber in a living organism, the conductance signal indicative of the volume of the chamber; conditioning the conductance signal to separate a noise portion of the conductance signal comprising the electrocardiogram signal from a conductance portion of the conductance signal; and extracting the electrocardiogram signal from the noise portion.

BRIEF DESCRIPTION OF THE DRAWINGS

An embodiment of the invention will now be described by way of example only with reference to the appended drawings wherein.

DETAILED DESCRIPTION OF THE INVENTION

Figure 1:
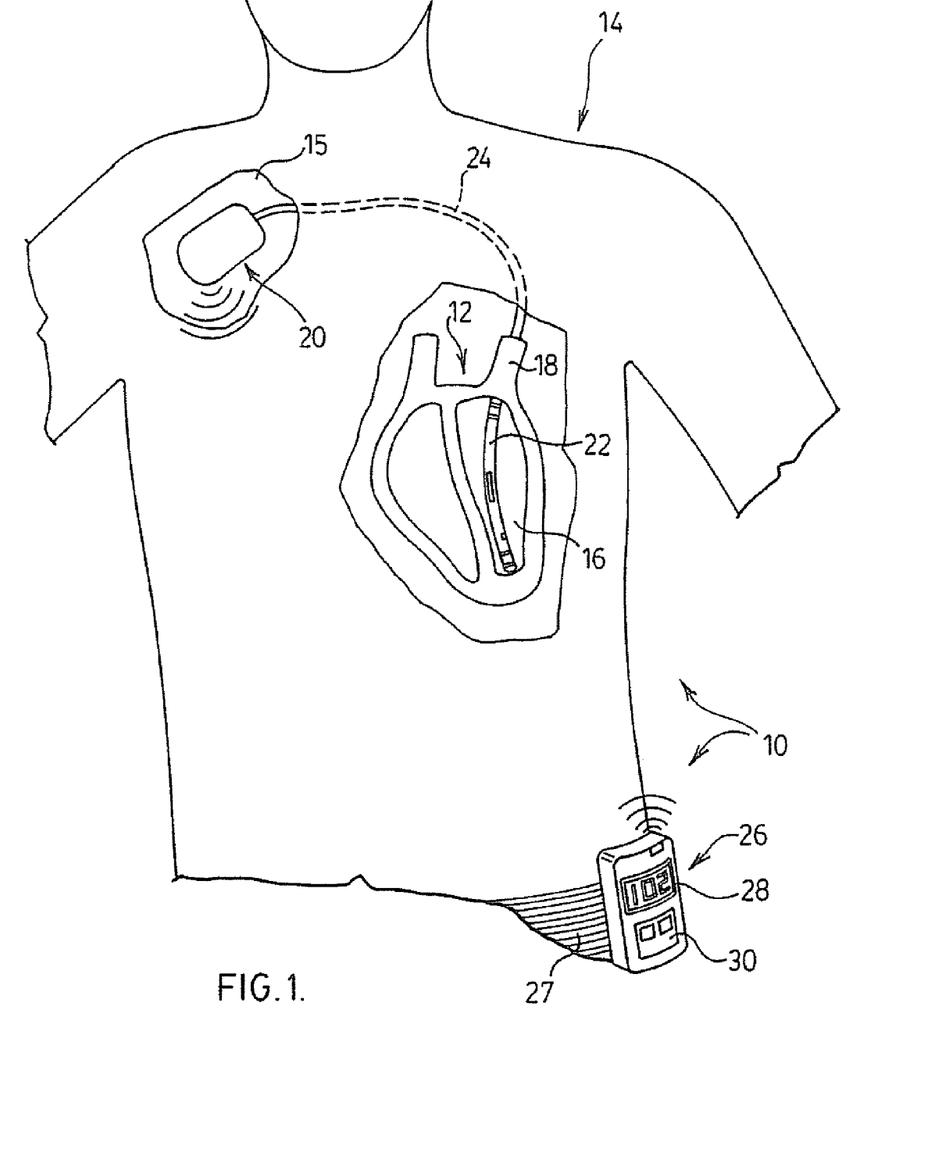
FIG. 1 pictorially shows a wireless cardiovascular data acquisition system.

Referring therefore to FIG. 1, one embodiment of a wireless cardiovascular data acquisition system is generally denoted by numeral 10. The system 10 operates to measure physical parameters of a heart 12 located within a body 14. The heart 12 and body 14 form part of a living organism, such as a gene altered mouse or a human. The heart 12 includes a heart chamber, in this example a Left Ventricle (LV) 16 that in part communicates with the body 14 via a heart valve 18. A sensing tip 22 is situated in the LV 16 by insertion thereof through the valve 18, and has a communication path 24 leading to a transmitting device 20 implanted in a portion 15 of the body 14, which in this example is external to the heart 12. In the example shown in FIG. 1, the portion 15 is in proximity of the body's clavicle. It will be appreciated that the transmitting device 20 may be situated anywhere as desired, e.g. within the heart 12 or heart chamber (i.e. LV 16).

The transmitting device 20 wirelessly transmits data to a receiving device 26 that in this example is attached to a belt 27 external to the body 14. The receiving device 26 may display data on a screen 28 as shown in FIG. 1, and may comprise a keypad 30 for scrolling between different views. A schematic of the system 10 is shown in FIG. 2.

Figure 2:
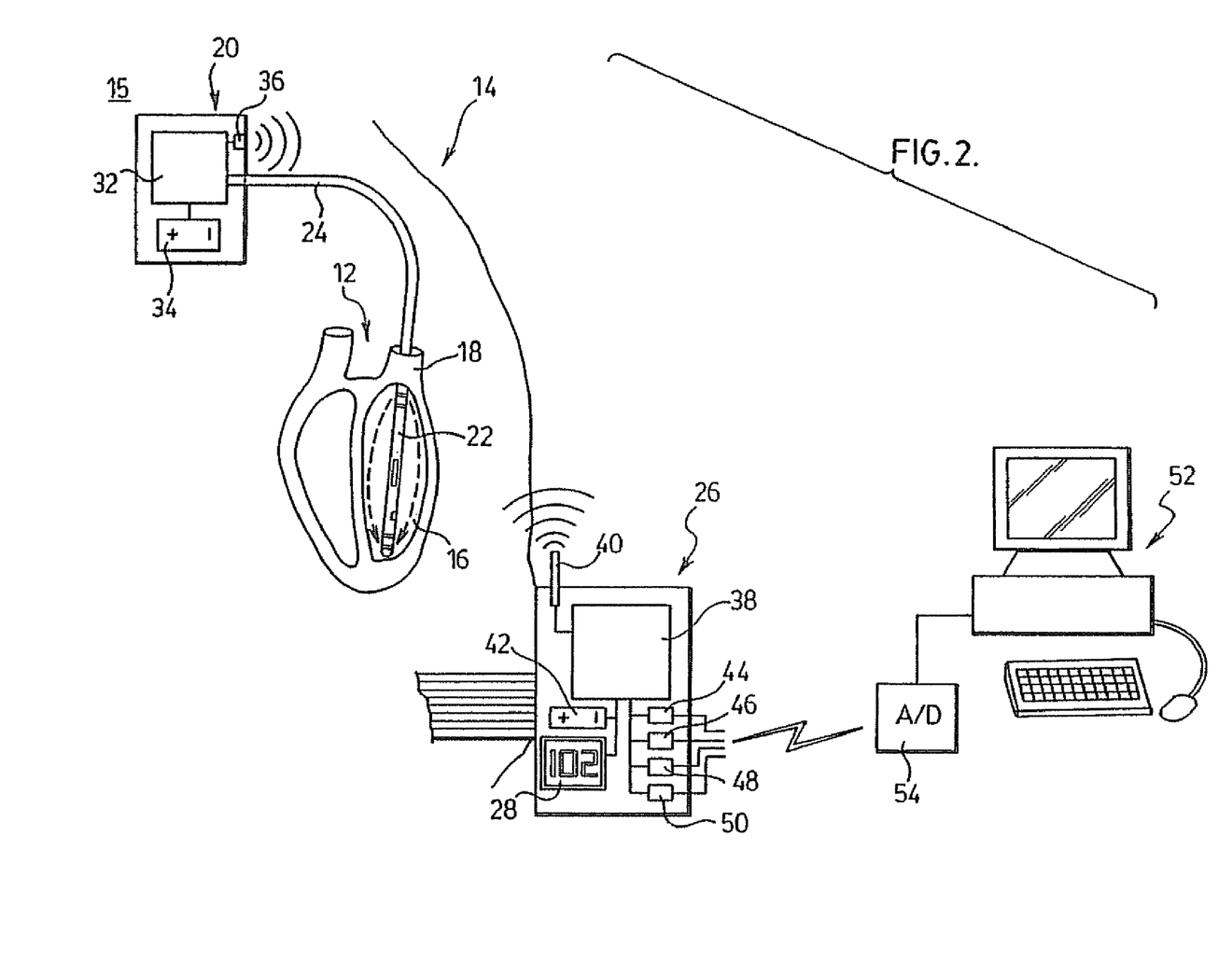
FIG. 2 is a schematic representation of the system of FIG. 1.

Referring now to FIG. 2, the path 24 communicates data acquired by the sensing tip 22 to a transmitter processing module 32 in the transmitting device 20. The transmitting device 20 is powered by obtaining energy from a battery 34, and has a transmitter 36. It will be appreciated that the use of a battery 34 is for illustrative purposes only and that any suitable means for powering the transmitting device 20 may be used such as power scavenging (converting environmental energy into electricity) or RF power transmission (energy transmitted to the device 20 from an external source through a radio frequency signal).

Since the processing module 32 is preferably implanted in the body 14, the signal sent via the transmitter 36 should pass through body tissue before reaching the air. The attenuation of an RF signal by different body materials is typically highly frequency dependent. Therefore, the transmitter 36 should be selected so as to minimize the attenuation of the signal it transmits. Typically, a lower frequency is preferred to transmit the signals since the lower the frequency, the greater the depth of penetration. However, the lower the frequency, the higher the wavelength and thus the longer the antenna required at the receiving end. Therefore, the transmitter 36 should be chosen to balance these requirements depending on the particular application. A suitable frequency to achieve such a balance is 40 MHz. The power consumed by the transmitter 36 should also be considered so that it can be faithfully detected at its receiving end whilst conserving energy.

The transmitting device 20 communicates wirelessly with the receiving device 26 through a receiver 40. The device 26 has a receiver processing module 38 that is adapted for processing data received from the device 20. The device 26 is powered by a battery 42 or suitable AC or DC power source (not shown). The device 26 has a series of signals (44-50) for providing electrical representations of measurements acquired using the sensing tip 22, including a pressure signal 44, a volume signal 46, a temperature signal 48, and an electrocardiogram (ECG) signal 50.

In FIG. 2 these signals are shown as being external to the processing module 38 and communicably connected to an external computing device 52 having an analog-to-digital (A/D) converter 54 connected thereto. However, it will be appreciated that the A/D converter 54 may be included in either the processing module 38 or processing module 32, and computing device 52 may be replaced by any suitable alternative such as processing capabilities provided by the processing module 38. The communicable link between the receiving device 26 and the computing device 52 and/or A/D converter 54 may be any hardwired or wireless communication channel, e.g., using Bluetooth technology.

The computing device 52, external or internal to the receiving device 26, may be any device that is capable of acquiring data and communicating with the processing module 38. In the example shown in FIG. 2, the device 52 is a standard personal computer (PC) having a monitor, central processing unit (CPU), keyboard, and mouse.

Figure 3:
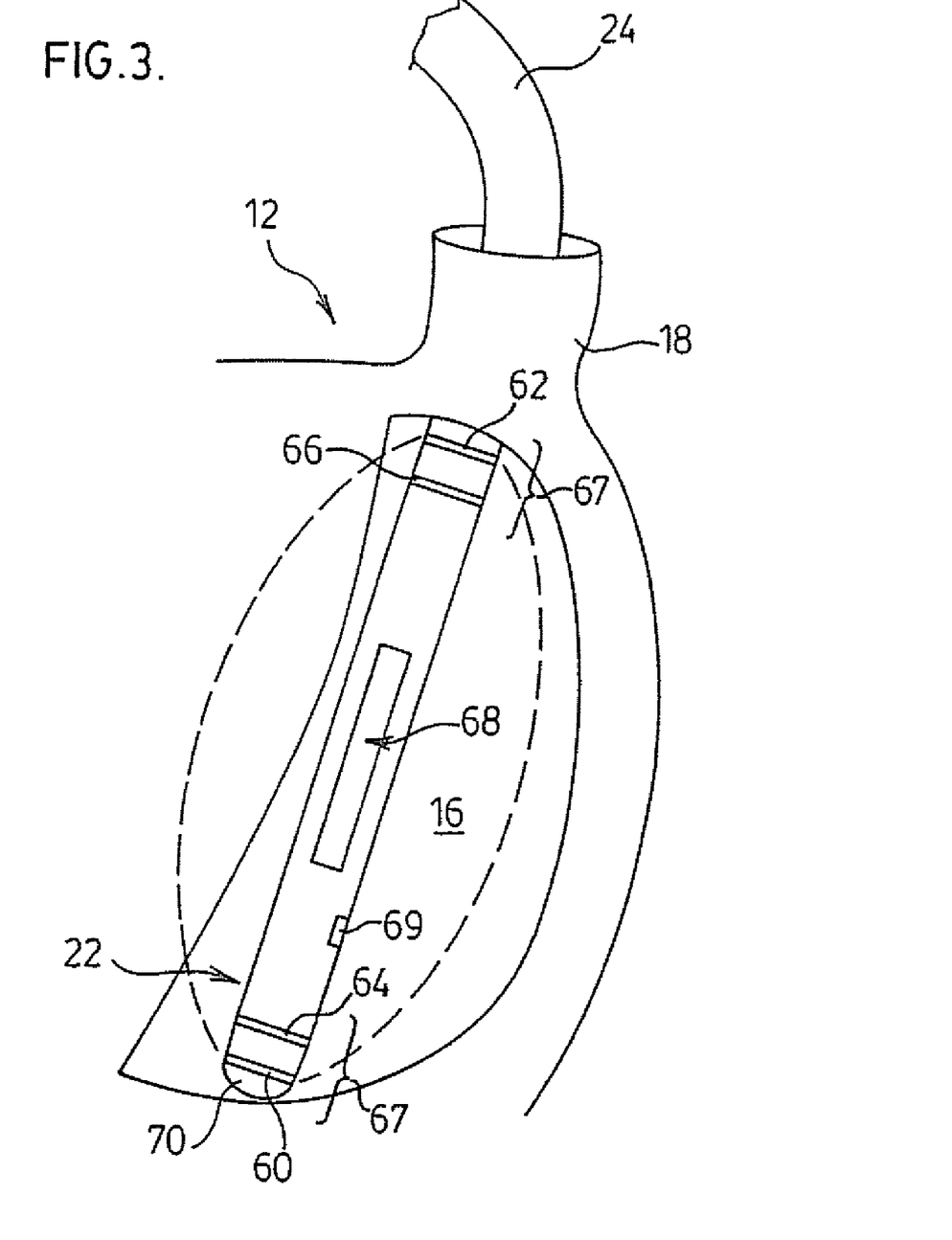
FIG. 3 is a magnified view of a portion the heart shown in FIG. 1.

The sensing tip 22 is shown in greater detail in FIG. 3. The sensing tip 22 has a rounded end 70 to facilitate the deployment thereof through the valve 18. In this example, a proximal electrode 62 and a distal electrode 60 each following the circumference of the sensing tip 22 flank a pair of inner electrodes 64, 66, a pressure sensing device 68, and a temperature sensing device 69. The electrodes 60, 62, 64 and 66 are used to measure the volume of blood in the LV 16 and are herein collectively referred to as the volume sensing device denoted by numeral 67. The proximal electrode 62 transmits a signal, and the distal electrode receives same to create an electric field in the LV 16. The inner electrodes 64, 66 sense this electric field to perform a conductance measurement indicative of the volume in the LV 16. The inner electrodes 64, 66 can be modeled conceptually as measurement probes on either side of a "resistor", wherein the "resistor" represents the resistivity of the blood in the LV 16, the inner electrodes 64, 66 are arranged to measure the potential across the "resistor". The volume measurement and/or volume signal may also be referred to as a conductance measurement and/or conductance signal respectively, and it will be appreciated that this terminology may herein be considered interchangeable.

The pressure sensing device 68 is used to sense the pressure of the blood in the LV 16. The temperature sensing device 69 is used to sense the temperature of the body 14, since it is substantially uniform throughout. The temperature sensing device 69 is preferably comprised of a thermistor or equivalent component. The volume sensing device 67, pressure sensing device 68, and temperature sensing device 69 communicate data to the transmitting device 20 through the path 24, thus the path 24 typically carries a number of wires, enabling data to be transmitted from the sensing tip 22 to the device 20. The length of the path 24 is dependent upon the location of the device 20 relative to the heart 12.

Although the temperature sensing device 69 is shown in FIG. 3 as part of the sensing tip 22, it will be appreciated that the device 69 may be situated anywhere in the body 14 enabling the internal temperature of the body 14 to be measured, and this may be inside or outside of the heart 12.

Figure 4A:
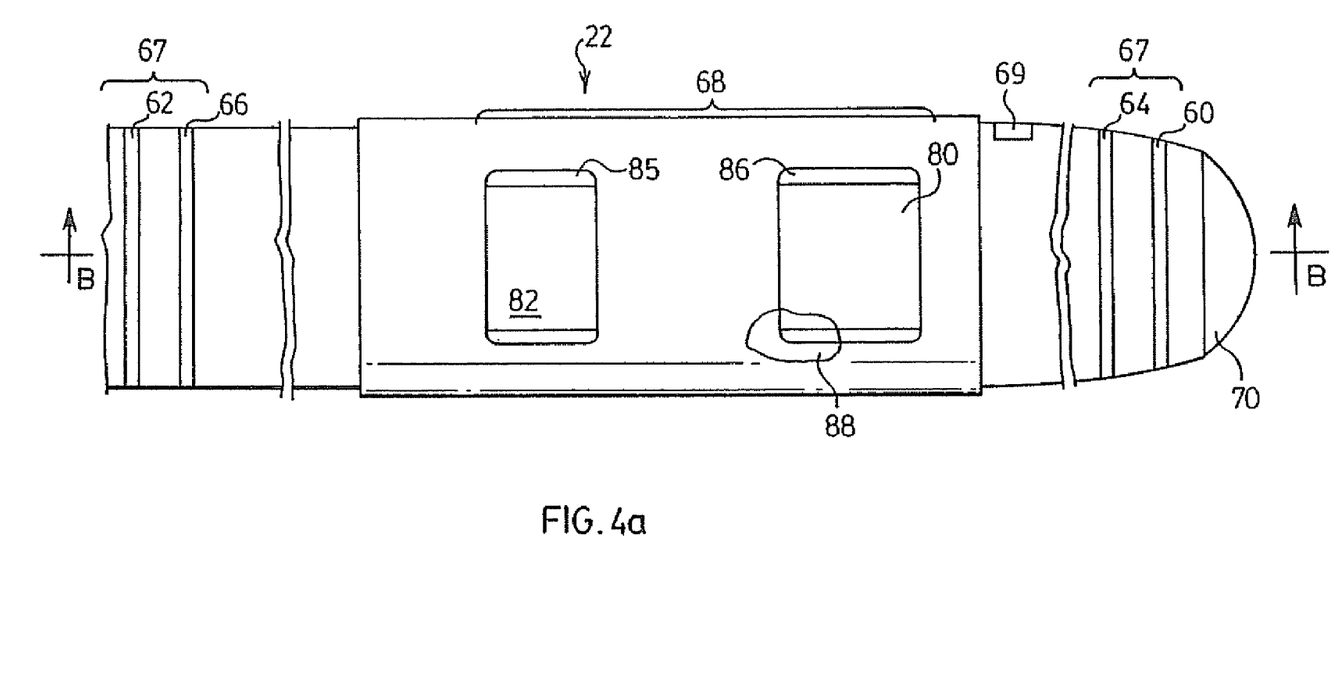
FIG. 4a is a partial plan view of the pressure sensing device of FIG. 2.
Figure 4B:
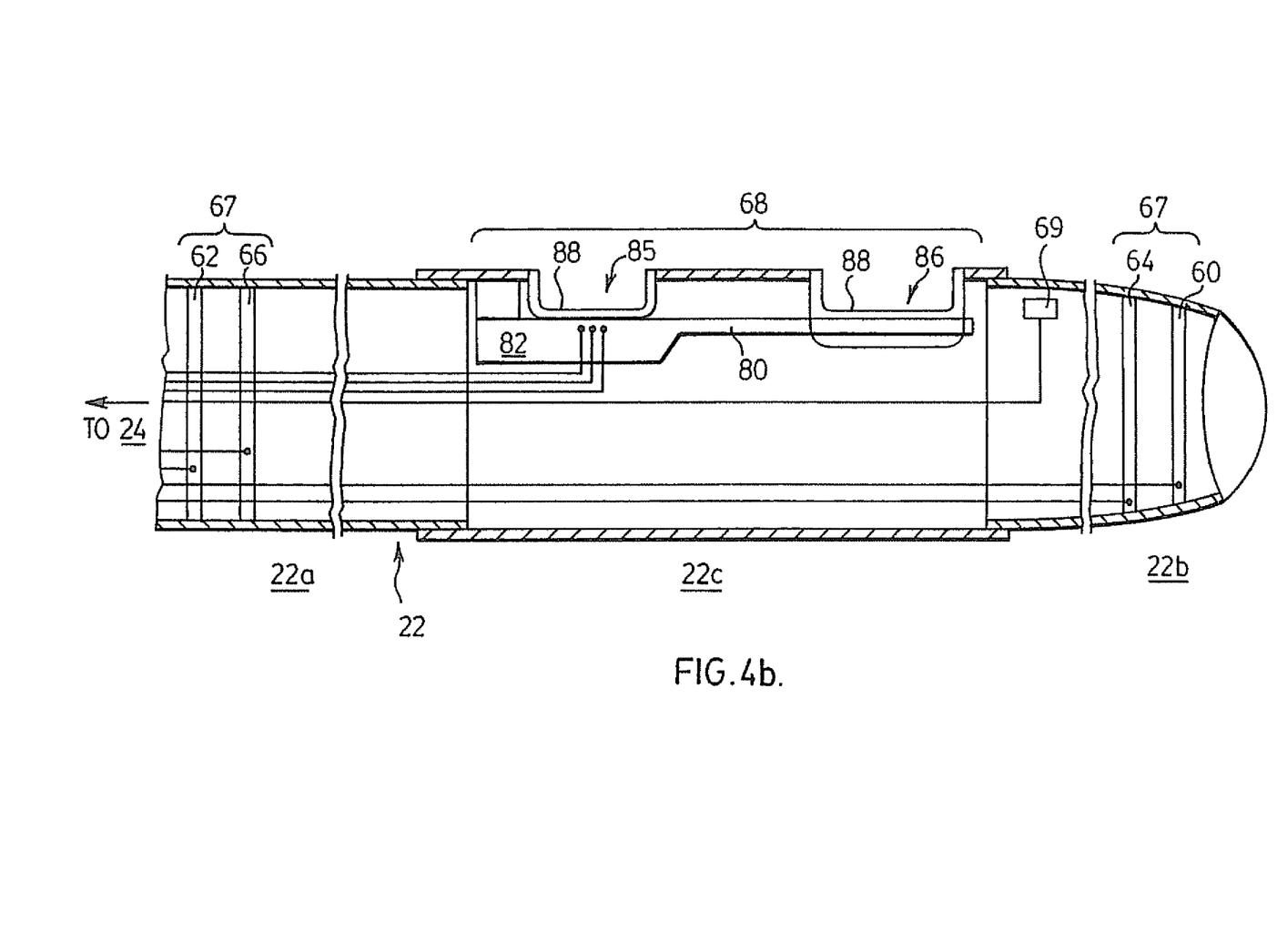
FIG. 4b is a sectional view of the sensing device shown in FIG. 4a along the line B-B.

An embodiment of the sensing tip 22 is shown in FIGS. 4a and 4b. It will be appreciated that the relative dimensions of the sensing tip 22 have been exaggerated for illustrative purposes only. The pressure sensing device 68 may be any device capable of sensing a pressure. In this example, the pressure sensing device comprises a piezoresistive deflection sensor, specifically a cantilevered sensor beam 80 having a base portion 82 that is attached to the housing of the sensing tip 22. A base window 85 in the sensing tip 22 enables the base of the beam 80 to experience external pressure, and a tip window 86 enables the tip of the beam 80 to experience external pressure. A layer of sealant 88 inhibits the beam 80 from direct contact with its surrounding environment. However, the layer 88 permits external pressure to effect flexure of the beam 80 due to variations in the pressure of the surrounding blood. It can be seen in FIG. 4b that electrical wires run from the sensing devices 67, 68 and 69 to the path 24.

Figure 5:
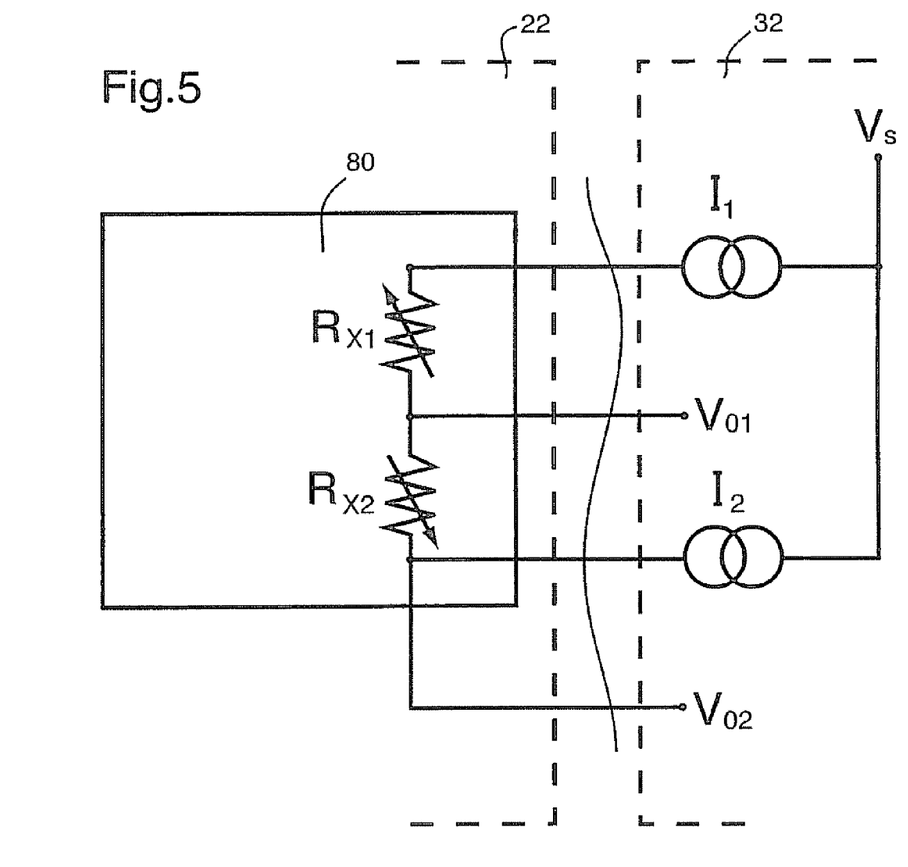
FIG. 5 is an electric schematic of the pressure sensing device.

An implementation of the beam 80 is shown schematically in FIG. 5, being a strain gauge sensor, on which two resistors $R_{x1}$ and $R_{x2}$ are mounted. When the beam bends as a result of a pressure experienced thereby, the resistances of these resistors change in opposite directions. That is, the resistance of one of the resistors increases while that of the other one decreases. As a result, the accompanying electronic circuits may be designed in a fully differential architecture which provides a higher signal to noise ratio (SNR) compared to a single ended architecture.

The following lists suitable specifications for the pressure sensing device 68, but shall in no way be considered limited thereto: nominal resistance of each resistor $R_{x1}$, $R_{x2}$ being 10,000 Ohms; gauge factor of 70-80; total resistor manufacturing tolerance of +/−10-15%; maximum resistance value mismatch between the resistors of 2.4%; temperature coefficient of resistance of +5%/100° F.; and a breakdown voltage of 20V.

These exemplary specifications illustrate that typically there may be non-idealities for the sensing device 68 that would preferably be addressed when designing the circuitry therefor. For instance, due to process variations, the resistances of $R_{x1}$ and $R_{x2}$ are in all likelihood not going to be equal. This may generate some offset at the output. Moreover, since the resistance of the resistors $R_{x1}$ and $R_{x2}$ is a temperature dependent parameter, the temperature coefficient of resistance (TCR) may cause an offset due to mismatch. Hence, even if the offset is cancelled at one temperature it may not be zero at another temperature. Finally, the temperature coefficient of the gauge factor (TCGF) makes the gain of the sensing device 68, temperature dependent.

The above parameters are typically sources for measurement inaccuracies. As a result, the output of the sensing device 68 may have some offset error and be dependent on temperature. In order to compensate for the above parameters, typically a signal conditioning scheme is utilized. In the example shown in FIG. 5, a Wheatstone bridge configuration is used to measure the resistance variations with two current sources $I_1$ and $I_2$.

As indicated above, $R_{x1}$ and $R_{x2}$ change in opposite direction as a function of strain or equivalently blood pressure in the heart as: $R_{x1}=R_{01}(1+GF.x)$ and $R_{x2}=R_{02}(1+GF.x)$ where $R_{01}$ and $R_{02}$ are the sensor resistances at zero strain, GF is the gauge factor of the sensing device 68, and x is the strain. The two current sources $I_1$ and $I_2$ complete the bridge, and are preferably integrated into the processing module 32 as shown in FIG. 5. In order to cancel out the resistor mismatch, TCR, and TCGF, the following equations should be valid: $R_{01}I_{02}-R_{01}I_{01}=0$; and $TCI=-(TCR+TCGF)$; where TCI represents the temperature coefficient of the current sources, $R_{01}$ and $R_{02}$ represent the resistor values at the reference temperature, and $I_{01}$ and $I_{02}$ represent the current of the two current sources at the reference temperature. The technology used to implement the processing module 32 should be capable of implementing a current source with any specific temperature coefficient, and the current sources should preferably be designed to have the lowest possible supply voltage sensitivity.

Figure 6:
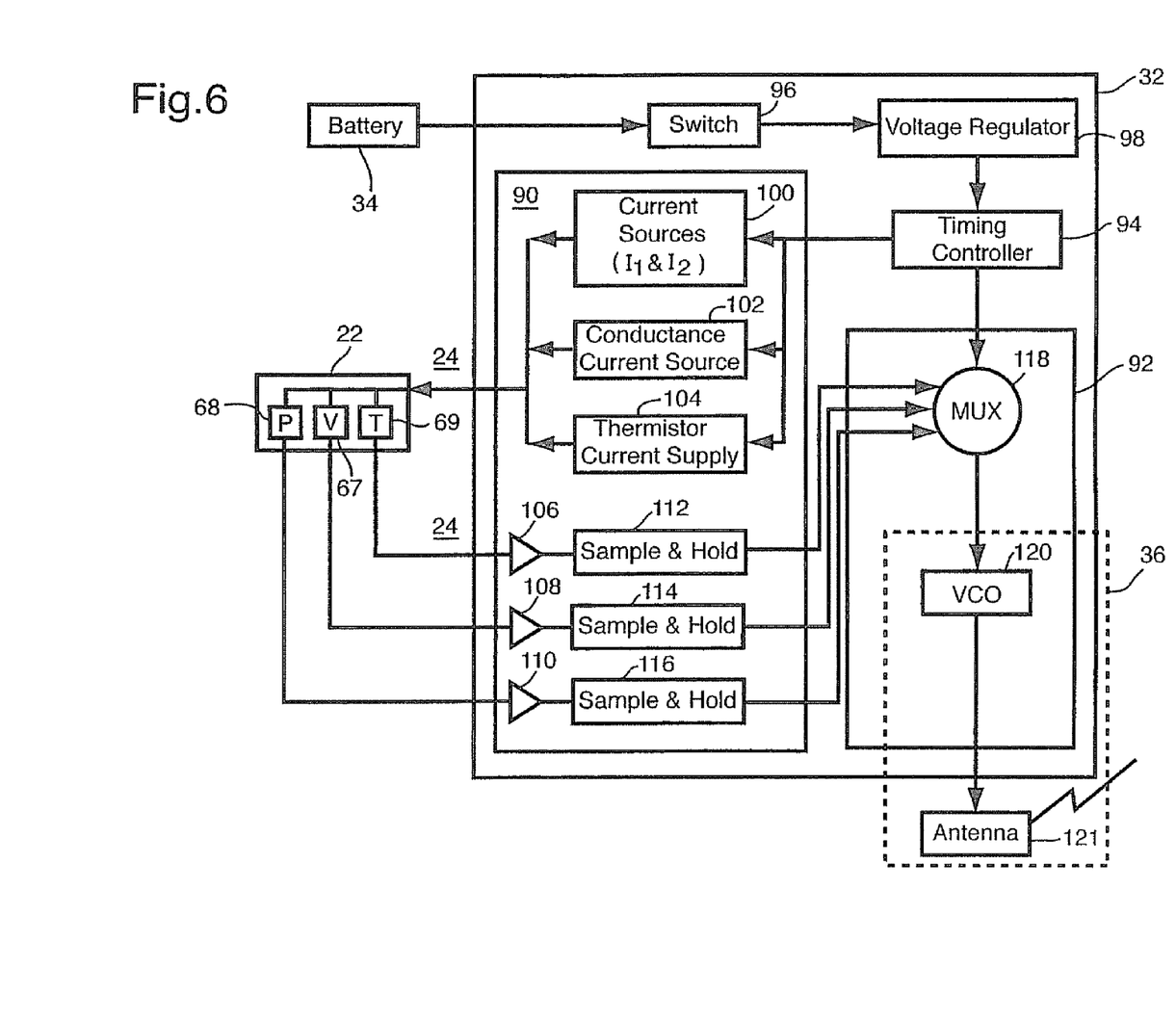
FIG. 6 is a schematic diagram of the transmitter processing module of FIG. 2.

A block diagram of the transmitter processing module 32 is shown in FIG. 6. The module 32 comprises a sensing block 90 and a transmitting block 92 controlled by a timing controller 94. The battery 34 which is connected to the module 32 may be controlled by a switch 96. The battery 34 is preferably a miniature battery of a suitable size and having a battery life that is as long as possible. A suitable battery has a life of 180 mAh, weight of 2.3 g, 1.5 Vdc, and a volume of 0.57 cc. The switch 96 may be, e.g., magnetic or radio controlled, i.e. any suitable device capable of controlling the main power to the module 32 from the battery 34. Between the timing controller 94 and the switch 96 is a voltage regulator that provides a regulated voltage to the timing controller 94 for controlling the blocks 90 and 92. With the above battery specifications, a suitable regulated voltage is a 1V output.

The sensing block 90 includes a current source block 100 for the pressure sensing device 68 (described above with current sources $I_1$ and $I_2$) to compensate for sensor non-idealities, and are the basis of temperature compensation for the pressure sensing device 68. The block 90 also includes a conductance current source 102 for generating the electric field using the electrodes 60 and 62; and a thermistor current supply 104 for the temperature sensing device 69, that preferably comprises a high resistance thermistor for minimal current drain. The outputs from these current sources (100-104) are sent to the sensing tip 22 over the path 24.

The measurements acquired by the sensing devices 67, 68 and 69 are sent back to the sensing block 90 over the path 24. The temperature signal is fed through an amplifier 106 and sampled and held for transmission by a sample and hold component 112. Similarly, the pressure signal is fed to an amplifier 110 and sample and hold component 116; and the volume signal is fed to an amplifier 108 and sample and hold component 114. The amplifiers 106, 108 and 110 are preferably used to encourage the fidelity of the signals. The sample and hold components 112, 114 and 116 hold the signal samples while the timing controller 94 switches power from the sensing block 90 to the transmission block 92.

The transmission block 92 has a multiplexer 118 and a voltage controlled oscillator (VCO) 120. The multiplexer 118 will read the samples from the blocks 112-116 and arrange the signals for transmission by the VCO 120. For example, the multiplexer 118 may arrange the signals in sequential order for transmission. The VCO 120 is connected to an antenna 121 and together make up the transmitter 36 shown in FIG. 2. A suitable VCO 120 is a Colpitts type that consumes an average current of 32 μA. The antenna 121 is preferably connected in parallel with the frequency determining inductor of the VCO 120, and preferably serves as an FM transmitter with a 42 MHz transmission frequency.

Figure 7:
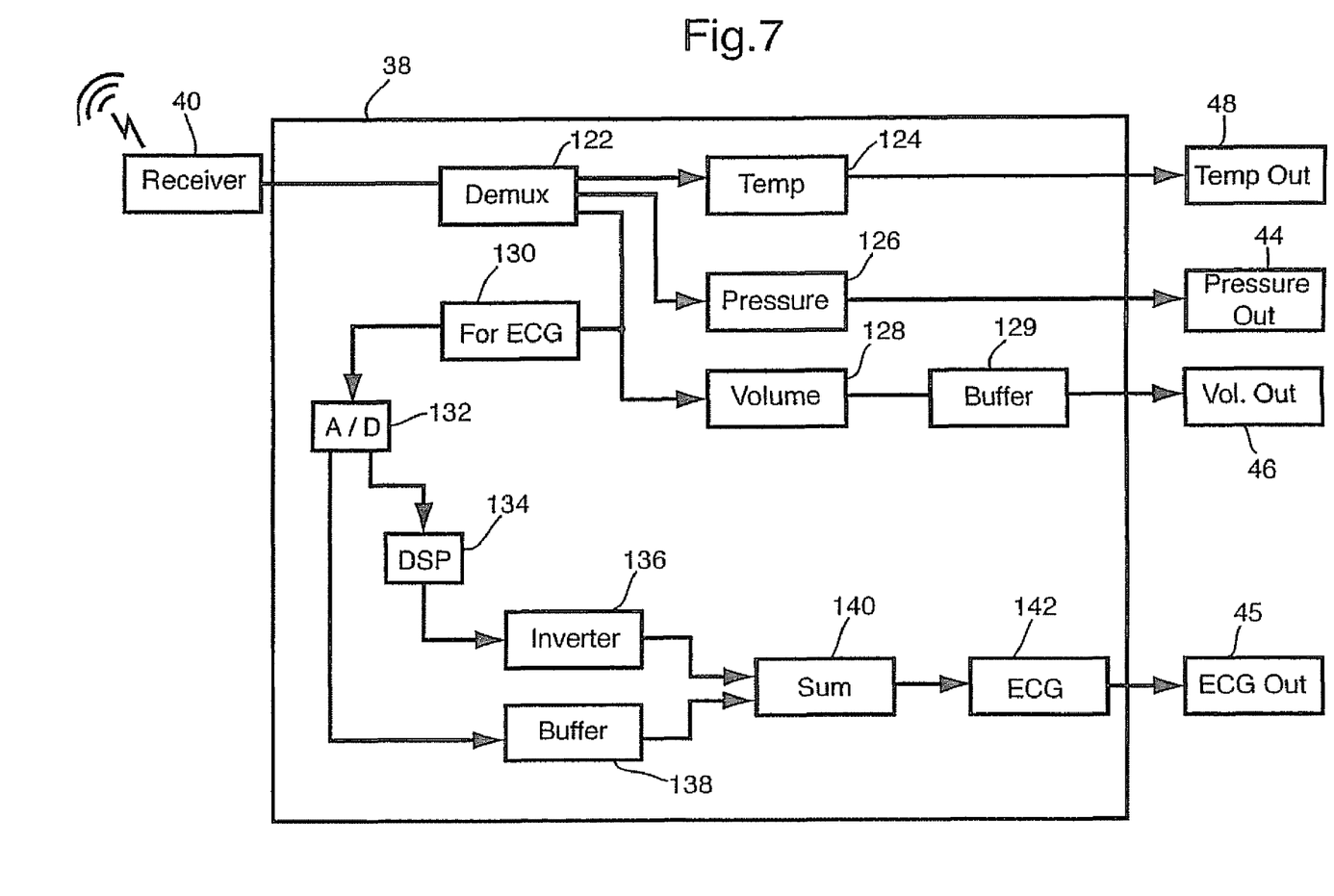
FIG. 7 is a schematic diagram of the receiver processing module of FIG. 2.

A block diagram of the receiver processing module 38 is shown in FIG. 7. The module 38 comprises a demultiplexer 122 connected to the receiver 40 of the receiving device 26. The demultiplexer 122 separates the signals that have been transmitted by the transmitter 36 and received by the receiver 40. If the signals are transmitted as analog signals, the demultiplexer 122 separates the received signal into individual analog signals, and in this example would provide three individual signals, a temperature signal 124, a pressure signal 126, and a volume signal 128. The temperature signal 124 may be immediately available as output 48, and the pressure signal 126 may be immediately available as output 44 for further processing and/or transmission to the computing device 52. It will be appreciated that the module 38 may also comprise a further internal component for processing and analysing the signals 124, 126 and 128, e.g., for display purposes. Moreover, the module 38 may comprise an alarm or other device to notify a wearer of the receiving device 26 of abnormal heart conditions. The display 28 may also be used with such additional processing to output heart parameters or a computed index that represents heart health.

The volume signal 128 may be sent through a buffer 129 and be available as output 46. The volume signal 128 may also be captured at block 130 for further processing to extract the ECG signal. This preliminary signal 130 is preferably converted using an analog-to-digital converter (A/D) 132, which enables signal manipulation while preserving the integrity of the original signal. It will be appreciated that the A/D 132 would not be needed if the signals received have already been converted to digital signals. The A/D 132 has two identical outputs, one of which is input to a digital signal processor (DSP) 134. The DSP 134 is used to clean the ECG signal from the volume signal, and allows for complex signal processing. The extraction of the ECG signal is described in greater detail later.

The signal emerging from the DSP 134 is inverted by an inverter 136. The inverter 136 may also be part of the DSP 134. The other output from the A/D 132 is buffered by the buffer 138 and the inverted signal and the buffered signal are summed at 140 to produce the ECG signal 142 that may also be available as output 45. The buffer 138 is used to maintain the synchronicity of the raw volume signal and the digitally manipulated version (i.e. by the DSP 134). The delay imposed by the DSP 134 would otherwise affect the results of the sum 140. The summer 140 adds the two volume signals, and since one has been inverted, the conductance part of the volume signal will be eliminated and the remaining signal will represent the ECG signal 142.

Figure 8:
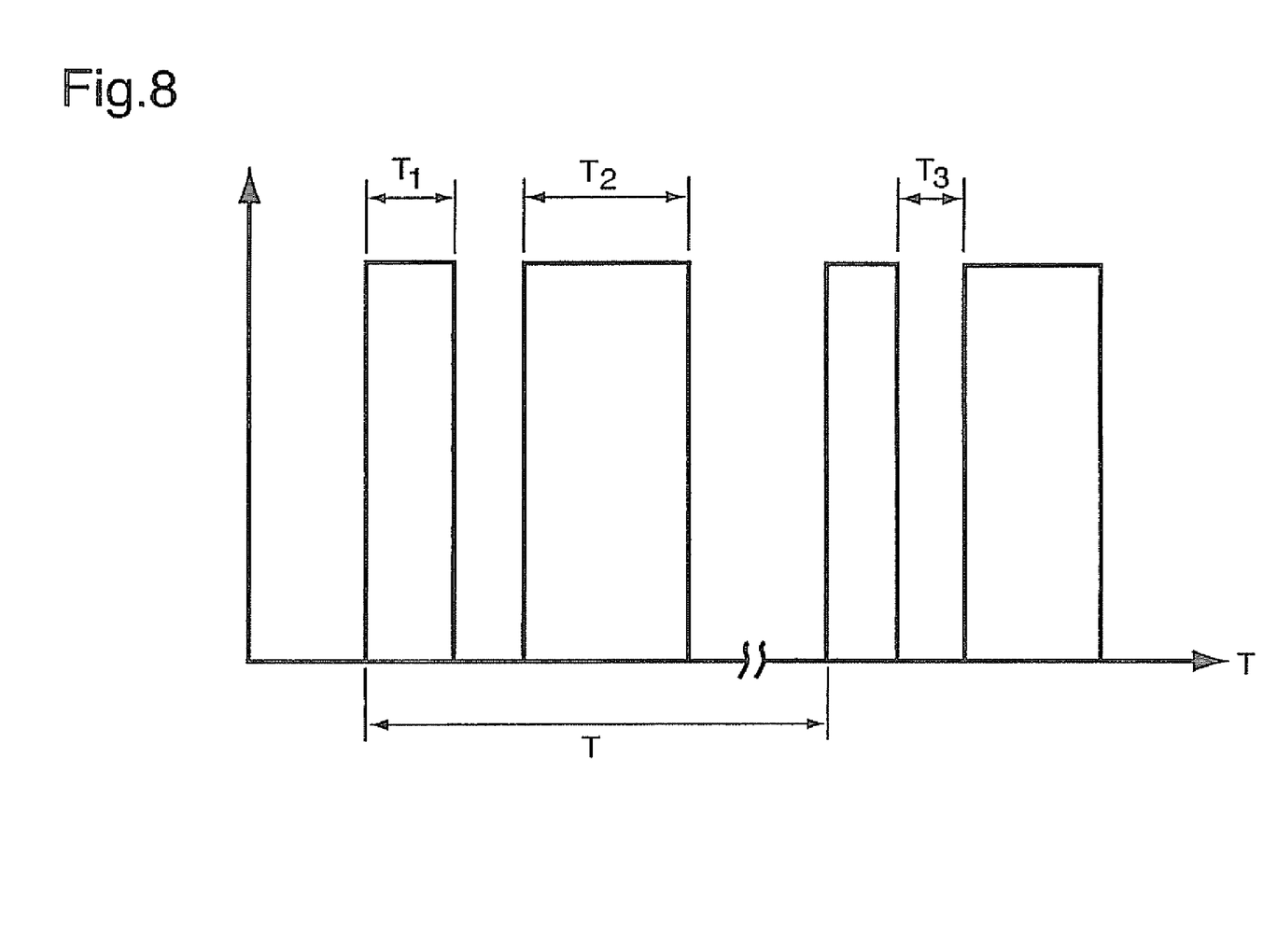
FIG. 8 is a timing diagram for the timing controller of FIG. 6.

The sensing block 90 and the transmitting block 92 are selectively powered using the timing controller 94 in order to conserve power. A timing diagram is shown in FIG. 8 illustrating the operation of the timing controller 94. The period T represents an entire monitoring cycle for the system 10 including measurement and transmission. Specifically, $T_1$ represents the period in which the sensing block 90 is powered in order to obtain the necessary measurements and sample and hold the signals; and $T_2$ represents the period in which the transmitting block 92 is powered in order to execute transmission of data from the transmitting device 20 to the receiving device 26.

For example, a 2 kHz sampling rate provides a period T of 500 μs to sample and transmit data. If the acquisition period $T_2$ is 20 μs, and transmission period $T_3$ is 50 μs, there exists 430 μs during each cycle, in which either the block 90 or the block 92 is waiting. The timing controller 94 uses this timing scheme to selectively turn off either the block 90 or block 92 that is not being used to conserver power, which provides an increase in battery life.

Another benefit arises from using such an energy saving timing scheme, namely the reduction of noise. Specifically, since the block 90 is powered whilst the block 92 is not, the transmitter 36 will not be affected by the noise generated by the signal conditioning, and, conversely, the sensing circuitry (block 90) will not be subject to noise from the transmitter 36. A 10 μs period, represented by $T_3$, is left between the end of one period and the beginning of the next, which enables any circuitry that needs stabilizing to do so.

Therefore, since the transmitting block 92 typically cannot transmit data that has not yet been collected, it would be wasting power while the sensing block 90 is performs its function. If the transmitting block 92 is turned off when it is not needed, power is not consumed, and thus conserved. Similarly, the sensing block 90 typically is not adding any data while the transmitter 36 is sending the previous sample, and thus does not need to consume power during that time.

Figure 9:
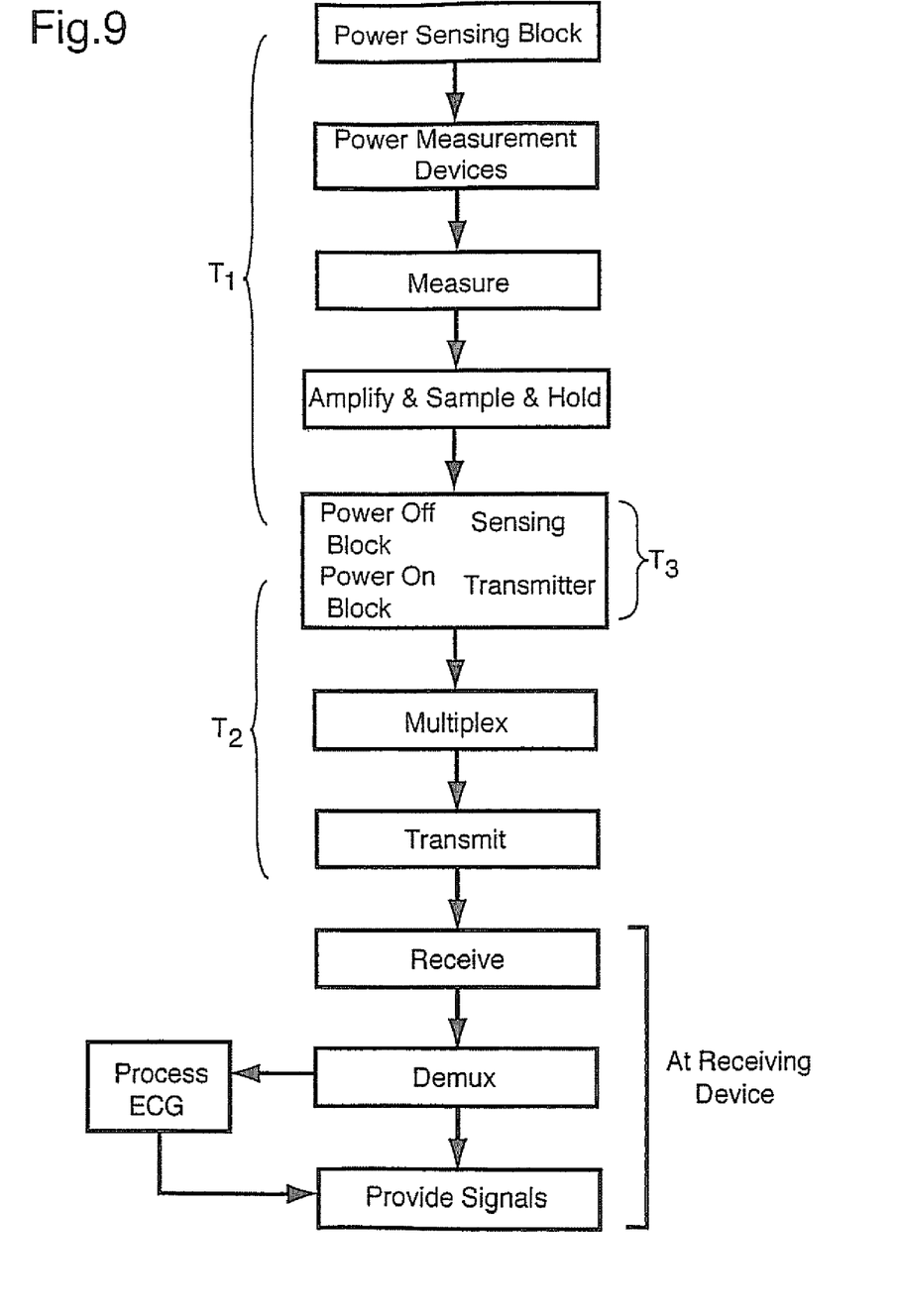
FIG. 9 is a flow chart showing an acquisition and transmission cycle.

FIG. 9 shows a flow chart illustrating an example of the steps taken by the system 10 during one complete cycle T, and the subsequent processing by the receiving device 26. The sensing block 90 is powered which enables the current sources to power the measurement devices 67, 68 and 69 and obtain the measurements. These measurements are then amplified and undergo a sample and hold. The sensing block 90 is then powered "off" and the transmitting block 92 is powered "on", wherein the time lag between theses steps is represented by $T_3$ as explained above. Once the block 92 has power, the multiplexer 118 is then able to obtain the signals stored in the sample and hold components 112-116, and combine these signals for transmission. In this example the multiplexer 118 preferably operates by arranging the signals in a particular sequential order that would be known to the demultiplexer 122 in order to enable the demultiplexer 122 to separate the signals at the receiving end.

The multiplexer 118 passes this "combined" signal to the VCO 120 that uses the antenna 121 to transmit the "combined" signal to receiving device 26. At this point, a complete measurement cycle has been executed, and the signal that has been transmitted continues to the receiving device 26 for further processing and/or output. The transmitting device 20 may then repeat this cycle as required or desired.

The receiving device 26 receives the "combined" signal from the receiver 40. The signal is passed to the demultiplexer 122 where it is separated into its components. The temperature and pressure signals 124 and 126 respectively, may be available as outputs or for further processing by the module 38. The volume signal 128 may be buffered and output at 46, and may also be obtained for extracting the ECG signal 142 and providing output 45. The extraction of the ECG signal 142 from the raw volume signal 128 is described in greater detail below, while referring to the functional blocks shown in FIG. 7 that relate thereto.

As indicated above, the conductance or volume signal 128 acquired using the volume sensing device 67 is used to extract the ECG signal 142.

The conductance signal acquired using the volume electrodes 67 consists of the conductance value of the blood in the LV 16, any noise generated by the system or in the environment, and the ECG signal 142 that is picked up as a component of environmental noise. As described above, in this example, the raw signals are collected and transmitted, e.g., as a combined analog waveform, without performing any signal conditioning, to the receiving device 26. When the combined signal is received by the receiving device 26, the individual pressure, volume and temperature signals (124, 126 and 128) are separated, and a process begins to separate the various components of the volume signal 128 (i.e. at 130).

The conductance signal 128 is the result of an electrical field generated, by means of the electrodes 60, 62, from the apex of the heart to the carotid artery. Due to myocardial contact of the conductance rings, the resulting conductance signal will also carry the ECG signal. It is generally common practice to use signal conditioning and filtering to eliminate the environmental and ECG noise components to extract the conductance signal 128. In this embodiment, signal conditioning is used to not only remove the ECG component of noise to extract the conductance signal, but also to separately condition the ECG signal 142 to remove the conductance portion of the signal. The result is that an ECG signal 142 can be collected without introducing any additional instrumentation into the LV 16. Therefore, the sensing tip 22 can be used to provide a more thorough cardiac assessment, using a single device.

Once the signal is obtained at 130, an A/D converter 132 in the processing module 38 converts the raw signal to a digital signal and passes the signal to each of an ECG digital signal processor (DSP) and a buffer 138. Once the respective signals are processed, they are summed and a final ECG signal 142 is produced.

Figure 10:
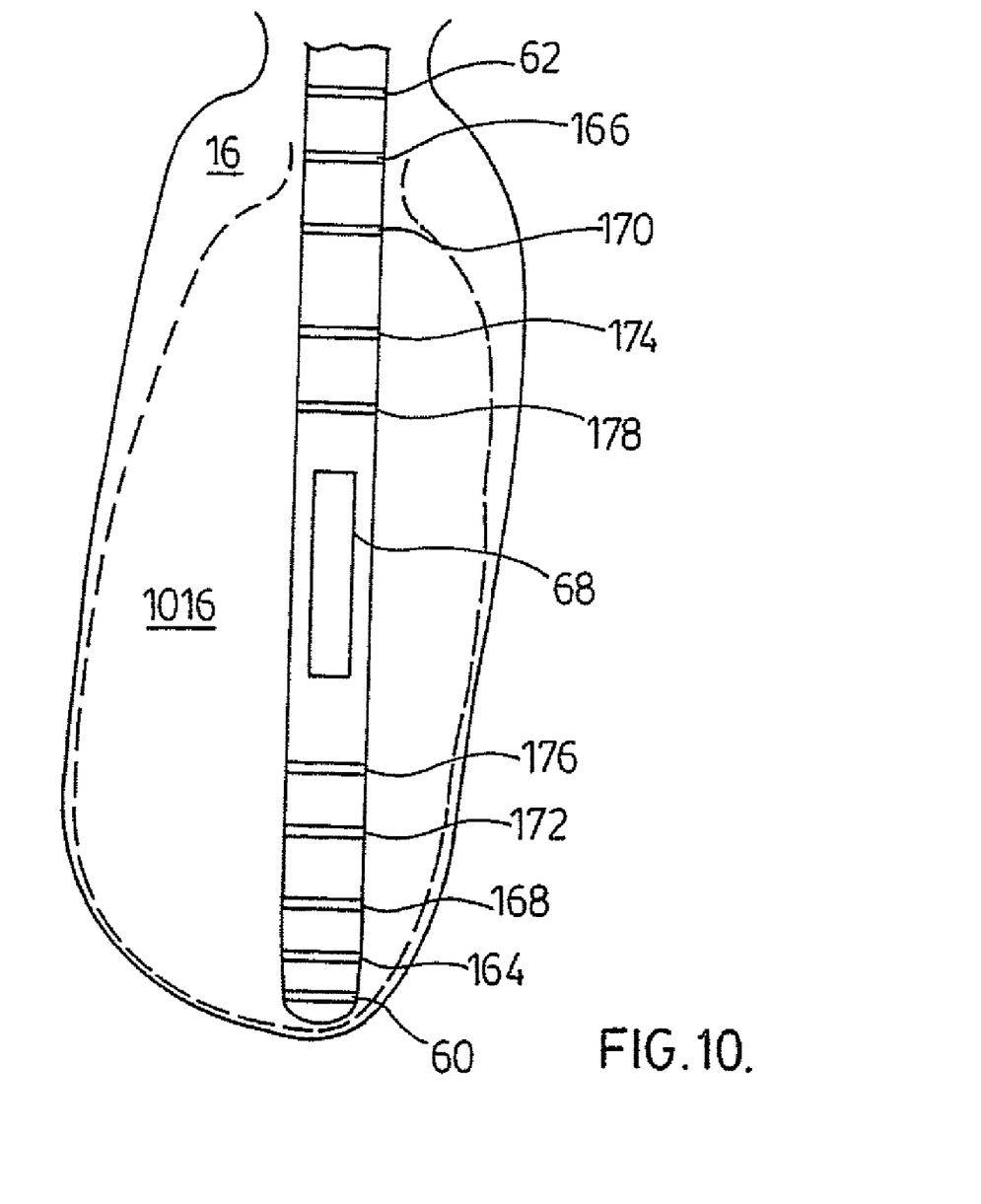
FIG. 10 shows another embodiment of the sensing tip of FIG. 3.

In another embodiment, the volume sensing device 67 comprises a plurality of inner electrode rings, for example four as shown in FIG. 10. Since the optimal conductance measurement is performed by transmitting along the entire length of the LV 16, and different organisms have different sized hearts 12, it may be desirable to incorporate multiple sets of inner electrode ring pairs. In FIG. 10, the LV 16 shown in FIG. 3 is provided, as well as an LV 1016 from a smaller organism shown in dashed lines. The pair 164, 166 is similar to the pair 64, 66 described above, however, the sensing tip 22 now includes the pairs 168, 170; 172, 174; and 176, 178 arranged progressively closer together and situated between the outer electrode pair 60, 62.

In such an embodiment, it may be possible to selectively operate any of the electrode rings as a transmitting ring, but typically the electrode 60 would remain as the receiving electrode. In the example shown in FIG. 10, the electrode 170 would be selected as the optimal transmitting electrode for the LV 1016 and then the inner sensing electrode pair would comprise the electrodes 164 and 174. Therefore, numerous configurations of receiving, and sensing electrodes can be selectively chosen in order to obtain an optimal conductance signal, depending on the size of the LV (e.g. 16 or 1016).

Therefore, the system 10 enables the monitoring of a heart in a living organism by measuring both pressure and volume in a chamber of the heart, preferably the LV 16. The pressure and volume measurements are acquired using a single sensing tip 22 and are communicated to a transmitting device 20 to be wirelessly transmitted to a receiving device 26, wherein they are used to monitor the heart. The system 10 may also incorporate a temperature measurement that can be transmitted with the volume and pressure measurement to provide further data for monitoring. The system 10 may also extract an ECG signal from the volume measurement. This allows the monitoring of up to four signals that can be used to determine the health of a heart.

In addition to a compact design, the system 10 may also incorporate an energy saving timing scheme that reduces the power required per acquisition cycle and thus increases the operational lifetime of the transmitting device 20.

Although the invention has been described with reference to certain specific embodiments, various modifications thereof will be apparent to those skilled in the art without departing from the spirit and scope of the invention as outlined in the claims appended hereto.

What is claimed is:

1. A method of monitoring a heart of a living organism comprising the steps of:
    establishing communication with a sensing tip situated within a chamber of said heart, said sensing tip comprising a pressure sensing device and a volume sensing device, wherein said pressure sensing device comprises a highly resistive strain gauge comprising a pair of resistors configured such that the resistances of said resistors change in opposite directions during operation of said pressure sensing device;
    obtaining a pressure measurement and a volume measurement in said chamber using said pressure sensing device and said volume sensing device respectively, wherein obtaining said pressure measurement comprises utilizing a signal conditioning scheme to compensate for non-idealities in said pressure sensing device by compensating for an offset caused by the temperature coefficient of resistance of the resistors and the highly resistive nature of said strain gauge using a pair of current sources;
    communicating said measurements to a transmitting device; and
    wirelessly transmitting electrical representations of said measurements to a receiving device, said electrical representations being used to monitor said heart.

2. The method of claim 1 wherein said transmitting device is located external to said heart.

3. The method of claim 1 further comprising the step of analysing said electrical representations to generate data indicative of the health of said heart.

4. The method of claim 3 wherein said data is a computed index based on said electrical representations.

5. The method of claim 3 wherein said data is displayed by said receiving device.

6. The method of claim 1 wherein said sensing tip extends along substantially the entirety of the longitudinal axis of said chamber.

7. The method of claim 1 wherein said pressure sensing device comprises a piezoresistive deflection sensor arranged on said sensing tip, said pressure measurement being sensed through flexure of said sensor.

8. The method of claim 1 wherein said volume sensing device comprises a first set of electrodes for transmitting and receiving an electrical signal through said chamber, said first set of electrodes being arranged at opposite ends of said sensing tip and flanking said pressure sensing device; and at least one set of inner electrodes for sensing said electrical signal transmitted and received by said first set of electrodes to obtain said volume measurement, said at least one set of inner electrodes flanking said pressure sensing device and being arranged between respective ones of said first set of electrodes and said pressure sensing device.

9. The method of claim 1 wherein said transmitting device is implanted into a portion of said living organism.

10. The method of claim 1 further comprising the step of transmitting said electrical representations to a computing device.

11. The method of claim 1 wherein said transmitting device operates by obtaining a supply of energy to enable continuous monitoring.

12. The method of claim 1 further comprising the steps of obtaining an internal temperature measurement using a temperature sensing device, communicating said temperature measurement to said transmitting device, and transmitting an electrical representation of said temperature measurement to said receiving device.

13. The method of claim 1 further comprising the step of obtaining an electrocardiogram measurement from said volume measurement by conditioning said volume measurement to separate a noise portion of said volume measurement comprising said electrocardiogram measurement from a conductance portion of said volume measurement, and extracting said electrocardiogram measurement from said noise portion.

14. A method according to claim 1 wherein said pair of resistors and said current sources are provided in a Wheatstone bridge configuration.

15. A method according to claim 1 wherein said current sources are chosen to have temperature coefficients that cancel out the temperature coefficient of resistance and the temperature coefficient of the gauge factor of said pressure sensing device.

16. A method according to claim 1 wherein said volume sensing device comprises at least three pairs of electrodes and obtaining said volume measurement comprises selecting a first set of electrodes for transmitting and receiving an electrical signal through said chamber according to the size of said chamber and selecting a second set of electrodes from others of said at least three pairs for sensing said electrical signal to obtain said volume measurement.

17. A method for obtaining an intracardiac electrocardiogram signal comprising the steps of:
   a computing device obtaining a measurement of a conductance signal taken from a heart chamber in a living organism using a volume sensing device, said conductance signal indicative of the volume of said chamber;
   said computing device conditioning said conductance signal to separate a noise portion of said conductance signal comprising said electrocardiogram signal from a conductance portion of said conductance signal; and
   said computing device extracting said electrocardiogram signal from said noise portion.

18. The method according to claim 17 wherein said electrocardiogram signal is extracted from said noise portion by said computing device inverting a conditioned conductance signal and summing said inverted conductance signal with said conductance signal obtained from said heart chamber.

19. The method according to claim 18 wherein said conductance signal obtained from said heart chamber is buffered while said conditioned signal is being generated by said computing device.

20. A method of monitoring a heart of a living organism comprising the steps of:
   establishing communication with a sensing tip situated within a chamber of said heart, said sensing tip comprising a pressure sensing device and a volume sensing device, wherein said pressure sensing device comprises a highly resistive strain gauge comprising a pair of resistors configured such that the resistances of said resistors change in opposite directions during operation of said pressure sensing device;
   obtaining a pressure measurement and a volume measurement in said chamber using said pressure sensing device and said volume sensing device respectively, wherein said volume sensing device comprises at least three pairs of electrodes and obtaining said volume measurement comprises selecting a first set of electrodes for transmitting and receiving an electrical signal through said chamber according to the size of said chamber and selecting a second set of electrodes from others of said at least three pairs for sensing said electrical signal to obtain said volume measurement, wherein obtaining said pressure measurement comprises utilizing a signal conditioning scheme to compensate for non-idealities in said pressure sensing device by compensating for an offset caused by the temperature coefficient of resistance of the resistors and the highly resistive nature of said strain gauge using a pair of current sources;
   communicating said measurements to a transmitting device; and
   transmitting electrical representations of said measurements to a receiving device, said electrical representations being used to monitor said heart.

21. The method according to claim 20 wherein said first set of electrodes comprises a distal electrode to be positioned at one end of said chamber and a proximal electrode chosen as the last electrode completely within said chamber upon placing said sensing tip in said chamber.

* * * * *

UNITED STATES PATENT AND TRADEMARK OFFICE
CERTIFICATE OF CORRECTION

PATENT NO. : 7,803,121 B2  Page 1 of 1
APPLICATION NO. : 11/207705
DATED : September 28, 2010
INVENTOR(S) : Peter Plouf et al.

It is certified that error appears in the above-identified patent and that said Letters Patent is hereby corrected as shown below:

On the Title Page, Item (75), "Mohammad Maymandi-Nejad" is deleted as an inventor of the claimed invention so that the corrected inventorship should read:

Peter Plouf
Blair Poetschke
Milan Placko
Kim Wood

Signed and Sealed this
Thirty-first Day of July, 2012

David J. Kappos
*Director of the United States Patent and Trademark Office*